(12) United States Patent
Ranieri et al.

(10) Patent No.: US 10,101,280 B2
(45) Date of Patent: *Oct. 16, 2018

(54) DEVICE AND METHOD FOR DETECTION OF COUNTERFEIT PHARMACEUTICALS AND/OR DRUG PACKAGING

(71) Applicant: The United States of America, as represented by the Secretary, Department of Health & Human Services, Washington, DC (US)

(72) Inventors: Nicola Ranieri, Maineville, OH (US); Mark R. Witkowski, West Chester, OH (US); Robert Hammaker, Manhattan, KS (US); William G. Fateley, Green Valley, AZ (US)

(73) Assignee: The United States of America, as represented by the Secretary, Department of Health and Human Services, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/332,908

(22) Filed: Oct. 24, 2016

(65) Prior Publication Data

US 2017/0038309 A1    Feb. 9, 2017

Related U.S. Application Data

(63) Continuation of application No. 13/262,371, filed as application No. PCT/US2010/029502 on Mar. 31, 2010, now Pat. No. 9,476,839.

(Continued)

(51) Int. Cl.
*G01N 21/95* (2006.01)
*G01N 21/23* (2006.01)
(Continued)

(52) U.S. Cl.
CPC ............. *G01N 21/95* (2013.01); *G01J 3/02* (2013.01); *G01J 3/0272* (2013.01); *G01J 3/10* (2013.01);
(Continued)

(58) Field of Classification Search
None
See application file for complete search history.

(56) References Cited

U.S. PATENT DOCUMENTS 5,245,179 A   9/1993   Chang et al.
5,479,258 A   12/1995  Hinnrichs
(Continued)

FOREIGN PATENT DOCUMENTS

EP   0999440 A1   5/2000
EP   1688851      8/2006
(Continued)

OTHER PUBLICATIONS

International Search Report and Written Opinion for PCT/US2010/029502, dated Jan. 11, 2011.

(Continued)

*Primary Examiner* — Frederick D Bailey
(74) *Attorney, Agent, or Firm* — Klarquist Sparkman, LLP

(57) ABSTRACT

Featured are a device (20) and method for the detection of counterfeit pharmaceuticals and/or packaging therefore. Counterfeit pharmaceuticals are detected by visual inspection upon exposing a suspected counterfeit pharmaceutical to one or more light sources having different wavelengths, and observing the differences in color and/or brightness between the suspected counterfeit and a genuine pharmaceutical/packaging. In further embodiments, a image acquisition device acquires an image showing color and/or other visual effect(s) brightness of the suspect counterfeit and this (Continued)

image is compared to an image of a authentic pharmaceutical/packaging.

22 Claims, 7 Drawing Sheets

Related U.S. Application Data

(60) Provisional application No. 61/165,395, filed on Mar. 31, 2009.

(51) Int. Cl.
*G06K 9/46* (2006.01)
*G01N 21/27* (2006.01)
*G06K 9/00* (2006.01)
*G06K 9/20* (2006.01)
*G01N 21/3563* (2014.01)
*G01N 33/15* (2006.01)
*G01J 3/02* (2006.01)
*G01J 3/10* (2006.01)
*G01J 3/32* (2006.01)
*G01J 3/50* (2006.01)
*G01N 21/33* (2006.01)
*G01N 21/64* (2006.01)

(52) U.S. Cl.
CPC . *G01J 3/32* (2013.01); *G01J 3/50* (2013.01); *G01J 3/501* (2013.01); *G01N 21/27* (2013.01); *G01N 21/33* (2013.01); *G01N 21/3563* (2013.01); *G01N 21/9508* (2013.01); *G01N 33/15* (2013.01); *G06K 9/00577* (2013.01); *G06K 9/2018* (2013.01); *G06K 9/4652* (2013.01); *G01N 21/64* (2013.01); *G01N 2201/0221* (2013.01); *G01N 2201/0627* (2013.01)

(56) References Cited

U.S. PATENT DOCUMENTS

| 6,535,637 | B1 | 3/2003 | Wootton et al. |
| 6,771,369 | B2 | 8/2004 | Rzasa et al. |
| 6,853,447 | B2 | 2/2005 | Goetz |
| 7,656,520 | B2 | 2/2010 | Cohn |
| 8,052,058 | B2 | 11/2011 | He |
| 2001/0016059 | A1 | 8/2001 | Krahn |
| 2002/0012895 | A1 | 1/2002 | Lehmann |
| 2003/0117620 | A1 | 6/2003 | Balas |
| 2004/0021861 | A1 | 2/2004 | Lewis et al. |
| 2004/0135086 | A1 | 7/2004 | Lewis et al. |
| 2004/0207842 | A1 | 10/2004 | Rzasa |
| 2004/0208373 | A1 | 10/2004 | Aoki |
| 2005/0108044 | A1 | 5/2005 | Koster |
| 2005/0243305 | A1 | 11/2005 | Vig et al. |
| 2005/0259254 | A1 | 11/2005 | Soller et al. |
| 2005/0264813 | A1 | 12/2005 | Giakos |
| 2006/0062734 | A1 | 3/2006 | Melker |
| 2007/0153512 | A1 | 7/2007 | Hendrie |
| 2007/0260487 | A1 | 11/2007 | Bartfeld et al. |
| 2007/0265880 | A1 | 11/2007 | Bartfeld et al. |
| 2008/0151112 | A1 | 6/2008 | Basile et al. |
| 2009/0002992 | A1 | 1/2009 | Dallas et al. |
| 2009/0023991 | A1 | 1/2009 | Gono |
| 2010/0110308 | A1 | 5/2010 | Nicholson et al. |
| 2011/0280480 | A1 | 11/2011 | Simske et al. |
| 2011/0293166 | A1 | 12/2011 | Sinbar et al. |
| 2012/0012750 | A1 | 1/2012 | Sinbar et al. |
| 2012/0098439 | A1 | 4/2012 | Recker et al. |

FOREIGN PATENT DOCUMENTS

| JP | 2008-282274 | 11/2008 |
| WO | WO 200067204 | 11/2000 |
| WO | WO 02/25568 A2 | 3/2002 |
| WO | WO 2003/060443 | 7/2003 |
| WO | WO 2005040739 | 5/2005 |
| WO | WO 2006/086085 | 8/2006 |

OTHER PUBLICATIONS

Intenrational Preliminary Report on Patentability for PCT/US2010/029502, dated Oct. 4, 2011.

Communication pursuant to Article 94(3) EPC issued by the European Patent Office dated Jan. 20, 2016, for corresponding EPC Patent Application No. 107284655, 8 pp.

Communication pursuant to Article 94(3) EPC issued by the European Patent Office dated Jul. 18, 2017, for corresponding EPC Patent Application No. 10728465.5, 8 pp.

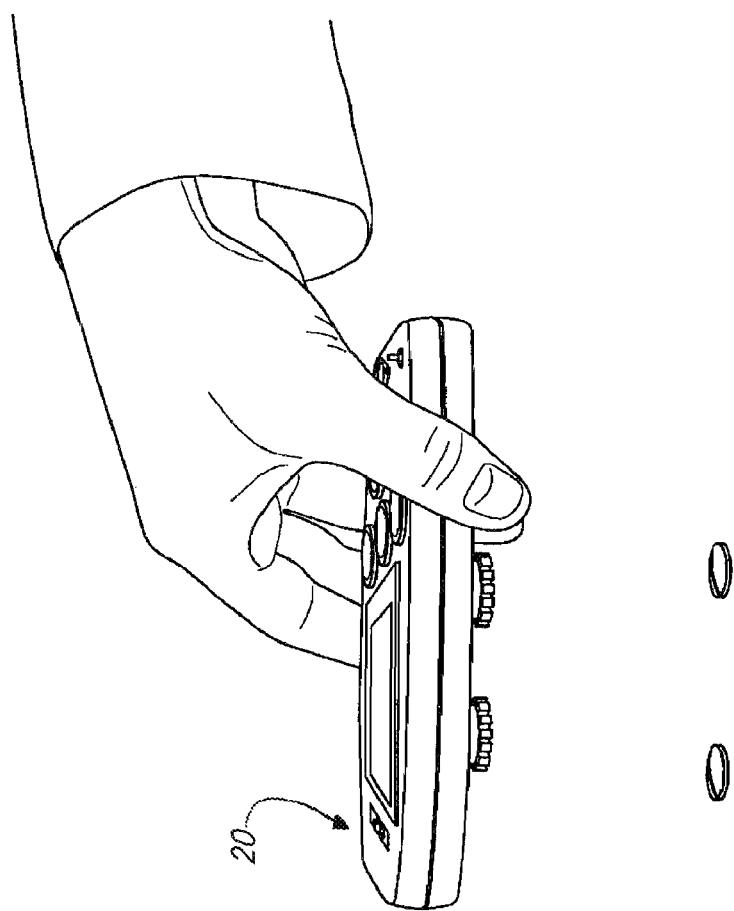

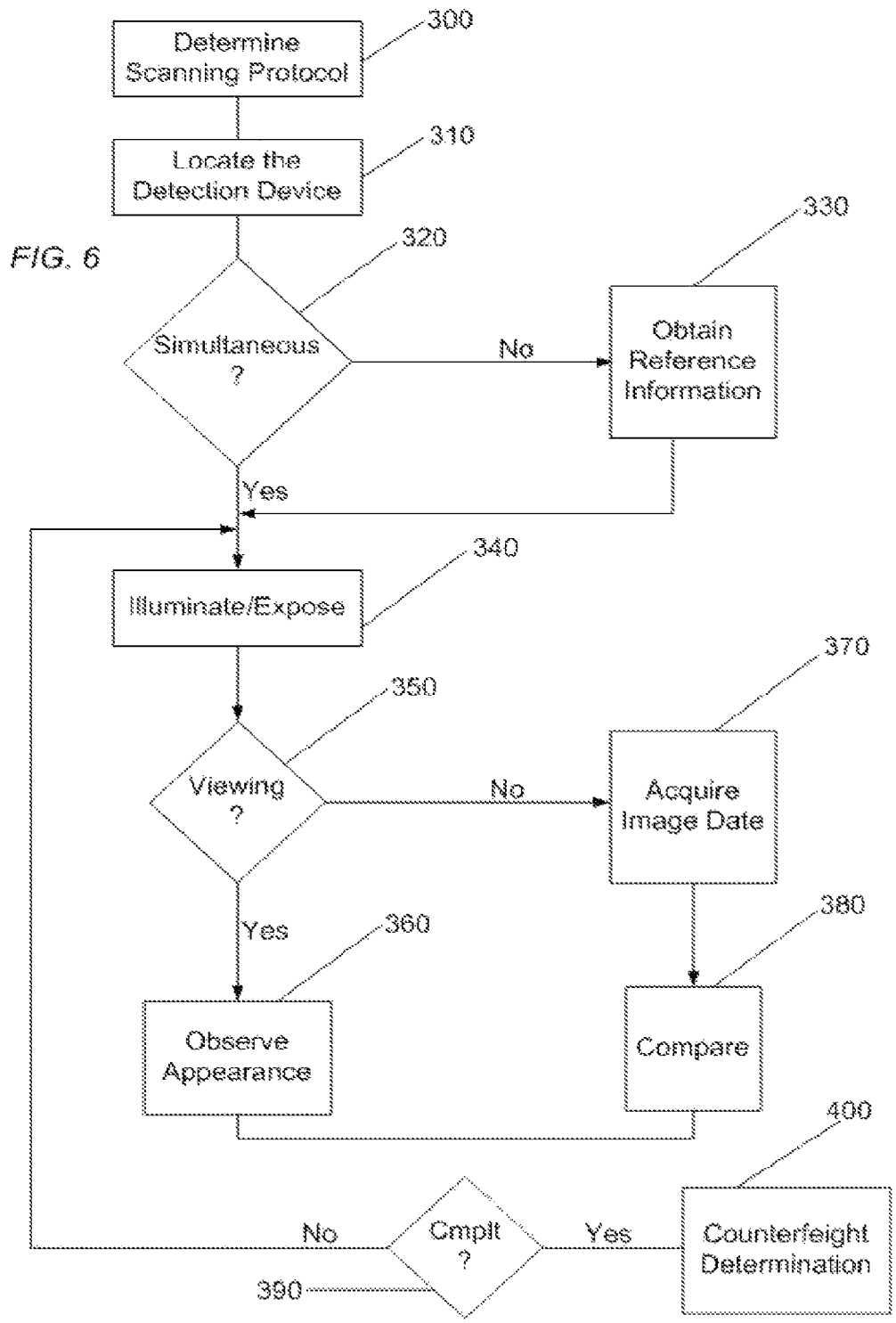

DEVICE AND METHOD FOR DETECTION OF COUNTERFEIT PHARMACEUTICALS AND/OR DRUG PACKAGING

CROSS-REFERENCE TO RELATED APPLICATIONS

This application is a Continuation application of pending U.S. patent Ser. No. 13/262,371, filed Sep. 30, 2011, now U.S. Pat. No. 9,476,839; which is a U.S. national entry of International Application PCT/US2010/029502 (WO 2010/120555) having an International filing date of Mar. 31, 2010, which claims the benefit of U.S. Provisional Application Ser. No. 61/165,395, filed Mar. 31, 2009; the entire contents of the aforementioned applications are hereby incorporated herein by reference.

FIELD OF INVENTION

The present invention generally relates to methods and devices for the detection of counterfeit pharmaceuticals and/or the packaging therefore and more particularly devices and method for detection of counterfeit pharmaceuticals and/or the packaging using visible and non-visible radiation and yet more particularly devices and method for in-situ detection of counterfeit pharmaceuticals using visible and non-visible radiation

BACKGROUND OF THE INVENTION

The amount of counterfeit pharmaceuticals entering the United States continues to increase. Such counterfeit pharmaceuticals are illegally imported into the United States, and are commonly available over the internet. It may be difficult to determine the authenticity of a pharmaceutical, since the genuine and counterfeit products may have nearly identical appearances and markings (e.g., shape, color, size, packaging, labeling, etc.), even when viewed by professionals. The detection of counterfeit pharmaceuticals is important, since the efficacy of a counterfeit product can be lower than the actual product. In addition, the counterfeit product may contain toxic components or other components that might result in side effects which are not associated with the real product. Also, such counterfeit products also result in severe monetary loss to pharmaceutical companies and retailers.

Current methods for detecting counterfeit pharmaceuticals include vibrational spectroscopy, x-ray diffraction, gas chromatography, liquid chromatography and mass spectrometry. These methods, although often effective, require expensive and bulky instrumentation, and are generally performed in a laboratory.

It thus would be desirable to provide a new device and methods for detecting counterfeit pharmaceuticals and/or packaging from the pharmaceuticals and/or packaging from an authorized manufacturer, supplier and the like. It would be particularly desirable to provide such devices and methods that would be portable and usable at any desired location such as the inspection point for customs. It also would be particularly desirable to provide such devices that would be hand-held and use visible and/or non-visible light to illuminate suspect pharmaceuticals and/or packaging and determining from such illumination if the pharmaceuticals and/or packaging being examined are counterfeit pharmaceuticals and/or packaging. Such detection devices preferably would be simple in construction and less costly than prior art devices and such methods would not require highly skilled users to utilize the device.

SUMMARY OF THE INVENTION

The present invention features a detection device that is configured and arranged so as to determine if an object is a counterfeit pharmaceutical product and/or package/packaging. In other aspects of the present invention there are featured methods for detecting a counterfeit pharmaceutical product and/or package/packaging.

Such a detection device includes a plurality of light sources configured to emit light at a plurality of different wavelengths so as to illuminate an object; at least one image acquisition device for receiving light returning from the illuminated object; and a means for determining from the returning light if the illuminated object is counterfeit. In illustrative embodiments, the object is a suspect pharmaceutical product (e.g., pill, capsule, cream, ointment, packaging components, etc.). As described further herein, a user can arrange an authorized or authentic product and/or packaging and the suspect product and/or packaging in proximity to each other so that the object being illuminated is both the authorized product and/or packaging and suspect product and/or packaging. As also described further herein, the user can use stored images of authentic product or packaging for comparison to the suspect product/packaging.

In further embodiments, the plurality of light sources include infrared wavelength(s), visible wavelength(s) and/or ultraviolet wavelength(s). In yet further embodiments, the plurality of light sources are LED light sources that emit radiation or light at or about the desired wavelengths.

In further embodiments, such a device further includes a display that is visible to a user which display provides an image output of the object being illuminated. In such an embodiment the image output provides a mechanism which the user can use to determine from the image output, that is representative of the light returning from the object, if the illuminated object is counterfeit. In the case, where the authorized product and the suspect product are being illuminated at the same time, the user can compare the respective image outputs to make such a determination.

In yet further embodiments, the detection device includes a controller that controls energization of the plurality of light sources so that one or more of such light sources are selectively energized to illuminate the object. In one particular embodiment, the controller is in the form of a plurality of switches (e.g., buttons, touch screen display) that control respective ones of the light sources. In another particular embodiment, the controller is configured so as to include circuitry or a processor with an applications program that are in turn configured and arranged so as to control the selective energization of one or more of the light sources based on an input from the user. Such input can be provided using any of a number of devices known to those skilled in the art such as, for example, buttons or a touch screen display.

In yet further embodiments, such a device can further include two or more image acquisition devices, each being configured and arranged so as to detect visible or non-visible radiation or light in different bandpasses or ranges. In particular embodiments, the image acquisition device embodies a CCD array as is known to those skilled in the art.

In yet further embodiments, the device includes one or more filters, that are arranged with respect to the one or more respective image acquisition devices so that the light returning from illuminated object is filtered before reaching the image acquisition device. In further particular embodiments, the one or more filters are configured so the returning light is filtered into a different bandpass. In yet further embodiments, a filter is provided for each image acquisition device.

In yet further embodiments, the image acquisition devices are operably coupled to the controller and the display is operably coupled to the controller, whereby the controller controls the displaying of the image based on the image data acquired from the image acquisition device.

In yet further embodiments, the detection device further includes a communication device that is operably coupled to the controller such that the controller can communicate acquired image data to an external device (e.g., computer) via the communication device. In an illustrative embodiment, the communication device is a USB port that allows direct communication between the detection device and the external device. In other embodiments, the communication device is any of a number of devices well known in the arts that allow communications between devices via, for example, a wide array network or a local array network, or the internet.

In yet further embodiments, the detection device includes a housing in which the above described functionalities of the detection device are housed for transport and use. In more particular embodiments, the housing is configured and arranged so as to maintain the plurality of light sources and the one or more image acquisition devices in fixed relation to each other.

According to another aspect of the present invention, there is featured a method for detecting a counterfeit pharmaceutical product and/or packaging therefore. More particularly there are featured methods for detecting such a counterfeit pharmaceutical product and/or packaging using light or radiation that is one or more of visible or non-visible light.

In particular embodiments, such a detecting method includes selecting a wavelength or wavelength range of light; exposing a suspected counterfeit pharmaceutical product and/or product packaging to light of the selected wavelengths; viewing the appearance of the suspected counterfeit product and/or product packaging upon exposure to the light; and comparing the appearance of the suspected counterfeit product and/or product packaging to the appearance of an authentic pharmaceutical product and/or product packaging exposed to light of the same wavelength or wavelength range. In the case where the appearance of the suspect product/packaging differs, one then determines if the suspect product is counterfeit. If the suspect product is determined using the devices and methods of the present invention to be counterfeit, it is within the scope of the present invention to perform additional testing to confirm such a conclusion.

According to another embodiment, of the present invention also featured is a method for detecting a counterfeit pharmaceutical product, including selecting a wavelength or wavelength range of light; exposing a suspected counterfeit pharmaceutical product and/or product packaging to light having of the selected wavelengths with a hand-held light source; viewing the appearance of the suspected counterfeit product upon exposure to the light; and comparing the appearance of the suspected pharmaceutical product to the appearance of an authentic pharmaceutical product exposed to light of the same wavelength or wavelength range. In such a method, the user is directly viewing the suspect product/packaging. In further embodiments, the method further includes wearing goggles whose lenses have been appropriately treated (e.g., filtered, colored, etc.) when viewing the pharmaceutical products.

In further embodiments, in such methods the wavelength of light is within the visible, ultraviolet or infrared range.

In yet further embodiments, such exposing includes exposing the suspected counterfeit product and an authentic product to the light simultaneously.

In yet further embodiments, such viewing includes comparing the appearance of the suspected counterfeit product to an image of the authentic product exposed to the same wavelength of light. In such methods, such comparing includes viewing the image of the authentic product one of before or after acquiring an image of the suspect product and/or product packaging. In such methods such comparing includes displaying the image of the authentic product and the acquired image such that the images are being viewed at the same time. In more particular embodiments, such methods further includes providing the image of the authentic product.

In yet further embodiments, the pharmaceutical product is a tablet or capsule.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 4 is a diagram of the counterfeit drug-detecting LED device in use with two tablets.

FIG. 6 is a high level flow diagram illustrating an embodiment of the methodology of the present invention.

DESCRIPTION OF THE PREFERRED EMBODIMENT

Figure 1:
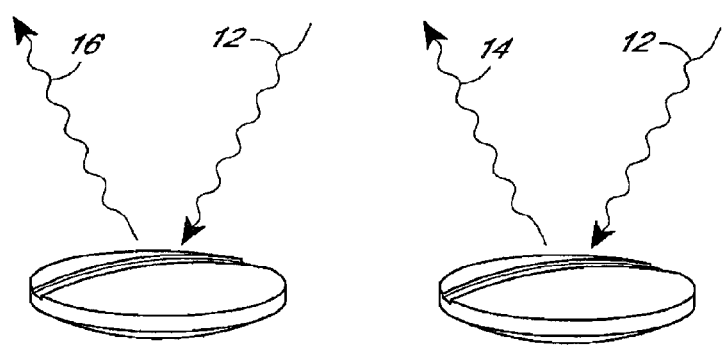
FIG. 1 is a schematic diagram illustrating the basic principle used in some advantageous embodiments of the invention.

The present invention in its broadest aspects includes devices and methods for the detection of suspected counterfeit pharmaceuticals including the packaging thereof. Such methods include exposing an authentic pharmaceutical and a corresponding suspected counterfeit pharmaceutical to one or more light sources having selected wavelengths and visually detecting a difference in color, brightness, contrast, darkening and/or other visual effect(s) between the authentic and suspected counterfeit pharmaceuticals. The device, embodying such methods, includes a plurality of light sources that generate the light to which the authentic and suspected counterfeit pharmaceuticals are exposed. In further embodiments, such light is generated using a hand-held, portable device and one or more LED (light emitting diode) comprise the one or more of the plurality of light sources.

As indicated above, the suspected counterfeit is visually observed when exposed to the light from the one or more light sources to determine if there is a difference in color and/or other visual effect(s), such as brightness, contrast, darkening, between an authentic pharmaceutical/packaging and the suspected counterfeit. Such differences occur because the light characteristics (e.g., light reflection, light absorption and fluorescence) are dependent upon the composition and makeup of the pharmaceutical and/or packaging. In other words, a difference in the composition or formulation between a counterfeit pharmaceutical and that for an authentic pharmaceutical can be revealed as a change in color and/or other visual effect(s) such as brightness, contrast, darkening, particularly when the two are exposed to different wavelengths of light and/or radiation. Similarly, differences in the materials used in the packaging components between the counterfeit and authentic packaging also should be visually observed when the two are exposed to different wavelengths of light/radiation.

It has been found that differences in color and/or other visual effect(s) such as brightness, contrast, darkening, are observable when authentic and counterfeit pharmaceutical products and/or product packaging are illuminated with appropriate wavelengths of light, and also when being observed through appropriate filters. Without being bound by any particular theory, it is believed that these differences in color and/or other visual effect(s) such as brightness, contrast, darkening, are produced by slight differences in the fluorescent response of the excipients (or other components) within the pharmaceutical product (e.g., tablet or capsule), in the inks on the products, or in the product packaging itself. It has also been noted that lot-to-lot variability in authentic pharmaceutical products in these properties are minimal since the production processes of such products are highly controlled. Thus, the appearance of different lots of such authentic pharmaceuticals will be very similar when viewed under different wavelengths of light. In contrast, suspect counterfeit products do not have a single source, are not controlled as highly in the various sources, and consequently have a greater variability in appearance and will generally appear different from authentic products and packaging.

Referring now to the various figures of the drawing wherein like reference characters refer to like parts, a schematic diagram illustrating the basic principle used in advantageous embodiments of the invention is shown in FIG. 1. As schematically illustrated, the incident light 12 impinges upon both a counterfeit and authentic pharmaceutical product (depicted in the figure as a tablet).

The intensity and wavelengths of the reflected light 14, 16 differs between the two products, resulting in an observable difference in color and/or other visual effect(s) between the two products and/or the product packaging. This observable difference occurs upon illumination with light of one or more particular wavelengths, which results in an observable difference in color and/or other visual effect(s). Also, differences that are not detectable by visually inspecting a pharmaceutical product with the naked eye under ambient lighting conditions are detected using the device and methods described herein. This principle is utilized in embodiments of the invention to produce an inexpensive and portable devices and screening methods for determining whether a pharmaceutical product of unknown origin is legitimate or not.

Figure 2A:
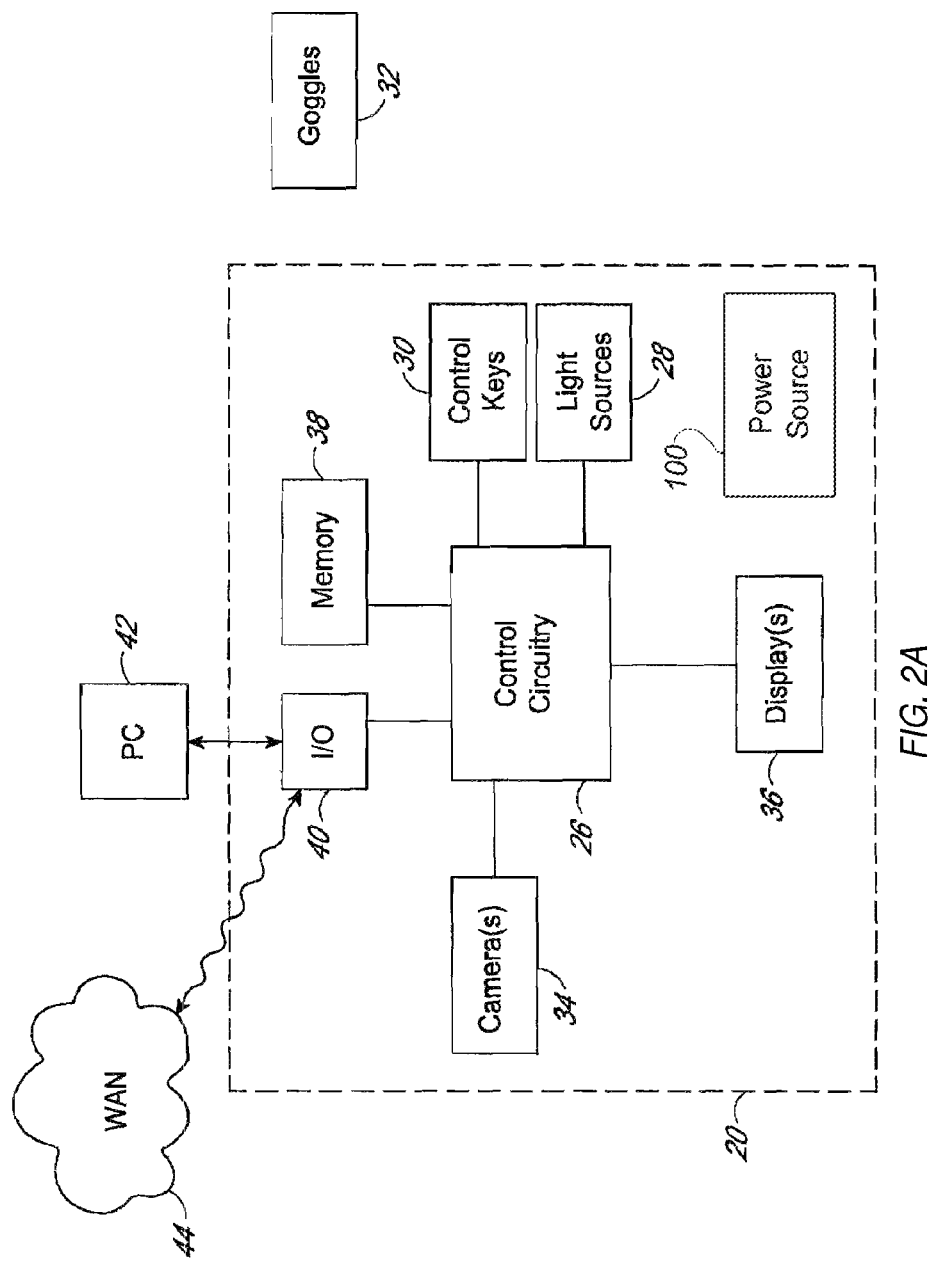
FIG. 2A is a schematic diagram of an embodiment of a counterfeit drug-detecting LED device of the present invention, including external applications.

Referring now to FIG. 2A, there is shown one embodiment of a counterfeit pharmaceutical detection device 20 according to the present invention. Such a device 20 includes control circuitry 26 that is composed of circuit components or elements that can carry out the functions described herein and/or such components along with a controller (e.g., a microprocessor, microcontroller, application specific integrated circuit (ASIC) or the like) or a controller. Such control circuitry 26 is configured and arranged so as to control the functionalities of the detection device including the light sources 28, display(s) 36 and the image acquisition device(s) such as a camera(s) 34.

In illustrative embodiments, such a device 200 also includes a plurality of switches, buttons or control keys 30 that are operably coupled to the control circuitry 26 that are used by the user for turning on or off one of more light sources 28. Alternatively, the detection device 20 embodies any of a number of other devices or techniques as is known to those skilled in the art that can control the selection of the one or more light sources. In an illustrative embodiment, the detection device display 36 is configured so as to emulate a touch screen having for example one or buttons displayed thereon each being representative of a light source. Thus, when a user touches one of the displayed buttons the control circuitry causes the corresponding light source to be turned on/off. In yet another embodiment, a touch pad is provided that controls a cursor depicted on the screen. By moving the cursor to one of the buttons depicted on the screen and actuating the touch pad, the user can cause a given light source to be turned on/off.

In yet further embodiments, the control circuitry 26 is configured so that when the a user provides an input indicating that the detection device is appropriately positioned with respect to the suspect product, the control circuitry includes instructions and criteria that controls the selection of the light sources, the turning of the light sources on/off as well as the sequence and which light sources to turn on/off, and the acquisition of image data using the appropriate image acquisition devices.

As described herein, the light sources are configured and arranged so as to have particular wavelengths that are used for the illumination of a pharmaceutical product and/or product packaging. As described herein, the illumination of the pharmaceutical products under specific wavelengths can produce a detectable difference in appearance (e.g., color and/or brightness) between a legitimate or authentic pharmaceutical product and a counterfeit pharmaceutical product. Thus, the light sources selected for use in illuminating at least the suspect product is done so as to use light sources having wavelengths that are likely to produce a detectable difference in appearance (e.g., color and/or brightness) between a legitimate or authentic pharmaceutical product and a counterfeit pharmaceutical product.

In some cases, the pharmaceutical product(s) are viewed by a user under the desired illumination (e.g., wavelength) through a filter, which can be incorporated into glasses or goggles 32 which filter out illumination wavelengths, and allow the wavelengths of the light or radiation returning from the illuminated product(s) to pass through. Although the different appearances of different products are not generally predictable a priori, with some experimentation, it has been found relatively easy to determine and document which illumination and filter wavelengths work well for distinguishing a given pharmaceutical product from a counterfeit version of that product.

Thus, it is within the scope of the present invention to establish criterion and operating protocols to follow that allow one to determine the type of light, the color of such light and any filtering requirements for viewing a suspect product to see if it is an authentic product. For example, it may be established from a series of experiments that, to determine whether an unknown tablet purportedly from Manufacturer A is counterfeit, the suspect product should be viewed under green light with a yellow filter, and in addition that when viewed in this manner, the color of the legitimate product has a bright yellow hue. Thus, when a suspect product when viewed under such conditions is a darker brownish and slightly red appearance, one can conclude that the suspect product is a counterfeit.

In yet further embodiments and for purposes of making the viewing more convenient and to potentially expand the observable emission spectrum, the detection device 20 further includes one or more image acquisition devices (e.g., cameras, CCD, night vision devices) 34 that are usable for imaging the pharmaceutical products under the desired illumination. In more particular embodiments, such image acquisition devices 34 are capable of detecting the light returning from the illuminated product or object and to provide an output representative of the detected light. For example, in a particular embodiment, an image acquisition device 34 is configured and arranged so it detects light at or about a predetermined wavelength corresponding to a given color of light and provides an output representative of the detected brightness of the light.

As described herein, such image acquisition devices 34 are further configurable with a filter or the like so the returning light is filtered so that the light impinging upon the sensing component(s) of the image acquisition device 34 is at or about the given wavelength. In illustrative embodiments, such image acquisition devices 34 comprise any of a number of devices that are known to those skilled in the art including, but not limited to a CCD camera or the like.

As indicated herein, the light illuminating the suspect product and the authentic product includes non-visible radiation or light such as light in the UV and IR ranges that are outside the human visual spectrum. In such cases, the image acquisition device includes a device (e.g., night vision devices) that are sensitive to light or radiation having such wavelengths. This expands the range of light usable for illuminating the suspect and authentic product and thus expands the range over which differences in appearance can be exploited.

In yet further embodiments, the image acquisition device 34 is configured so as to include an optical adjustment capability, such that the image acquisition device is usable as a "portable microscope" by using macro zoom capabilities of the incorporated lens(es). A hand held up-close viewing of the objects being illuminated while using such macro lens, allows for high resolution viewing.

In further embodiments such a detection device 20 includes a display 36 (e.g., LCD display) that is operably coupled to the control circuitry 26. In this way, when image data is acquired by a given image acquisition device, the control circuitry provides outputs to the display so as to thereby cause the display to provide an image having a color and brightness that is representative of the image data acquired or sensed by the given acquisition device. It also is within the scope of the present invention for the control circuitry 26 to combine image data from one or more image acquisition devices so that the display reproduces a color image representative of the color that would be observed as if it were being viewed by the eye. In sum, the display is usable for visually displaying images of the pharmaceutical product(s) under the selected wavelength(s).

The detection device also is configurable with a memory 38 such as a non-volatile or flash memory to store information for the operation of the detection device, image data representative of one or more authentic pharmaceutical products or packaging. In more particular embodiments, such information includes instructions regarding the appropriate wavelengths to use for various products and previously acquired images of authentic and counterfeit pharmaceutical products. Such information is intended to allow an agent in the field or in situ to easily compare the appearance of suspected counterfeit to the authentic product.

For example, an image of an authentic product is stored in the memory 38 which is retrieved from the memory by the control circuitry 26. The image data is sent to the display 34 so that the user can use the stored image as a reference image for comparison with the acquired image of the suspect product. The control circuitry 26 is configurable so that the stored image is displayed at least one of before or after the image of the suspect product is acquired. In further embodiments, the control circuitry 26 is configured so that both the stored image and the acquired image are displayed at the same time (e.g., side by side arrangement) much as would be seen if the detection device was illuminating the authentic and suspect products at the same time.

In yet further embodiments, the detection device 20 includes one or more communication devices or input/output devices 40 that allows communication between an external device such as for example a computer (e.g., personal computer) and the detection device. In this way, instructions, image data of authentic products or application program data/instructions can be downloaded to the detection device or previously acquired image data by others using such a device 20 either in a laboratory test environment or in the field can be downloaded to or from the detection device. Such an I/O device 40 includes a USB port or communication device, a network I/O device that allows communications over a wide area network (WAN) or a local area network (LAN) either using wireless or wired communication techniques.

Such a detection device 20 also includes a power source 100 that is operably coupled to the functionalities of the detection device and under the control of the control circuitry 26. Such a power source is any of a number of sources of electrical power as is known to those skilled in the art and including for example rechargeable or non-rechargeable batteries (e.g., alkaline, lithium ion, metal hydride and the like) and capacitors or high power capacitors. Such power sources 100 also can further include any of a number of electrical functionalities known to those skilled in the art (e.g., transformers) so as to control the power (voltage, current) being outputted by the power source so as to be at or about an appropriate value. In more particular embodiments, the detection device 20 is constructed so as to made in a hand-held form and be portable. In further illustrative embodiments, the power source is a battery such as a 12 VDC portable battery, or is any center polarity power adapter (e.g., 12-15 VDC).

Figure 2B:
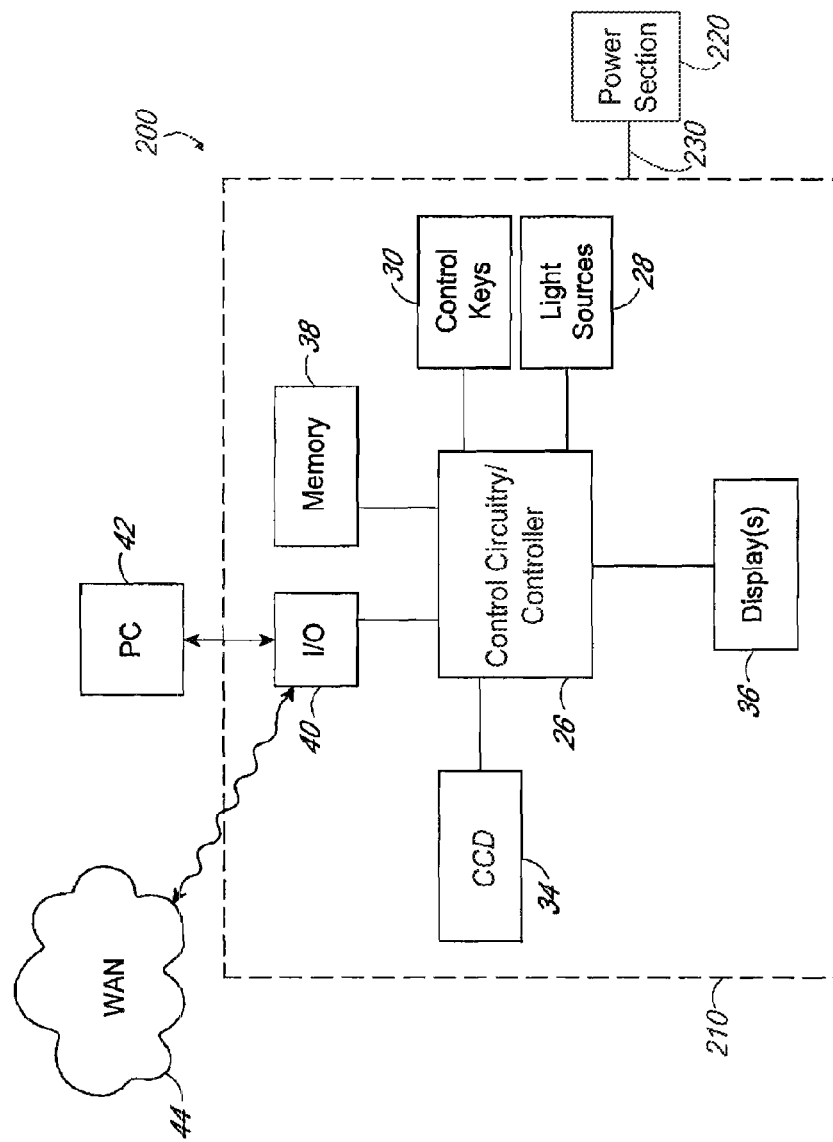
FIG. 2B is a schematic diagram of another embodiment of a counterfeit drug-detecting LED device of the present invention, including external applications.

Referring now to FIG. 2B there is shown a detection device 200 according to another embodiment of the present invention. Reference shall be made to the discussion above regarding FIG. 2A for details of devices or functionalities having common reference numerals. In this embodiment, the detection device 200 includes two sections, a scanning section 210 and a power section 220 that includes a power source 100. The power section 220 is operably coupled to the scanning section 210 by a cable 230 so that the power source supplies the power to operate the scanning section. In this arrangement, the scanning section 210 is configured and constructed so as to be made in a hand-held form and be portable. Such a power section 220 need not be configured or made so as to be hand-held but can be configured so as to be portable or fixed so as to provide a larger power source. For example, in an illustrative embodiment, the power section 210 is belt mounted so as to be worn about the waist of the user.

The devices and methods described herein are particularly well suited for field work, such as that done by Customs agents at airports, inspection stations and other ports of entry into the United States. In particular, this is the case as the detection device 20 or scanning section 210 are configurable so as to be made in a hand-held form and portable.

Figure 3A:
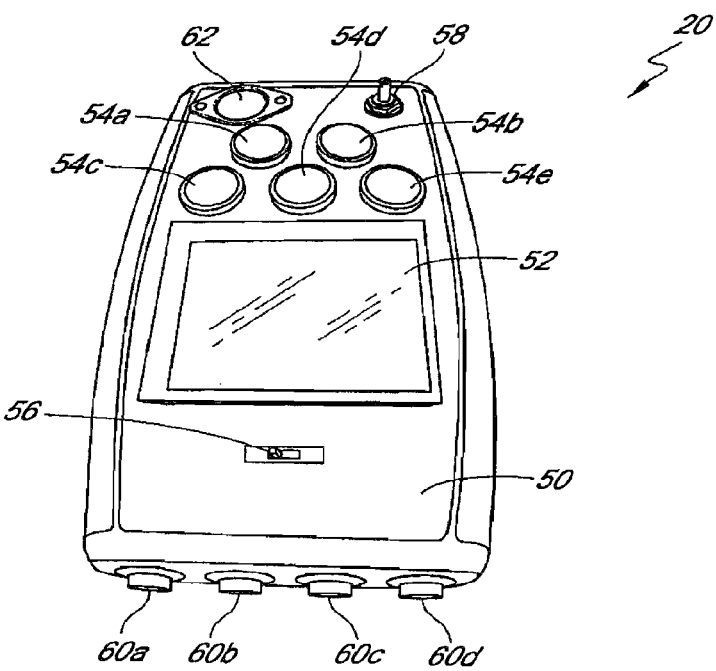
FIG. 3A is a top view of one embodiment of the counterfeit drug-detecting LED device of the present invention.

Referring now to FIGS. 3A, B there is shown a representative example of a hand-held detection device according to the present invention. It should be recognized that is well within the skill of those knowledgeable in the art to configure the detection device as described in any of the embodiments described herein as well as configuring a scanning section 210 so as to embody feature shown and described herein in connection with FIGS. 3A-B.

There is shown in FIG. 3A, a top view of the detection device 20, which further includes a housing 50 in which various components of the device are disposed. One such component is an LCD display screen 52, which display allows the user to view images acquired by cameras 70*a*, 70*b* or other image acquisition devices described further below. Although the display will be described herein as producing a visible spectrum output, it will be appreciated that other image processing techniques can be used to provide a visible depiction or display of non-visible UV and/or IR wavelengths emitted by the product under view that are detectable only by the camera, whereby detectable differences can be found outside normal human vision capabilities. Depending on the product, this can enhance the differences seen between a legitimate and counterfeit product when viewed on the LCD display.

Figure 3B:
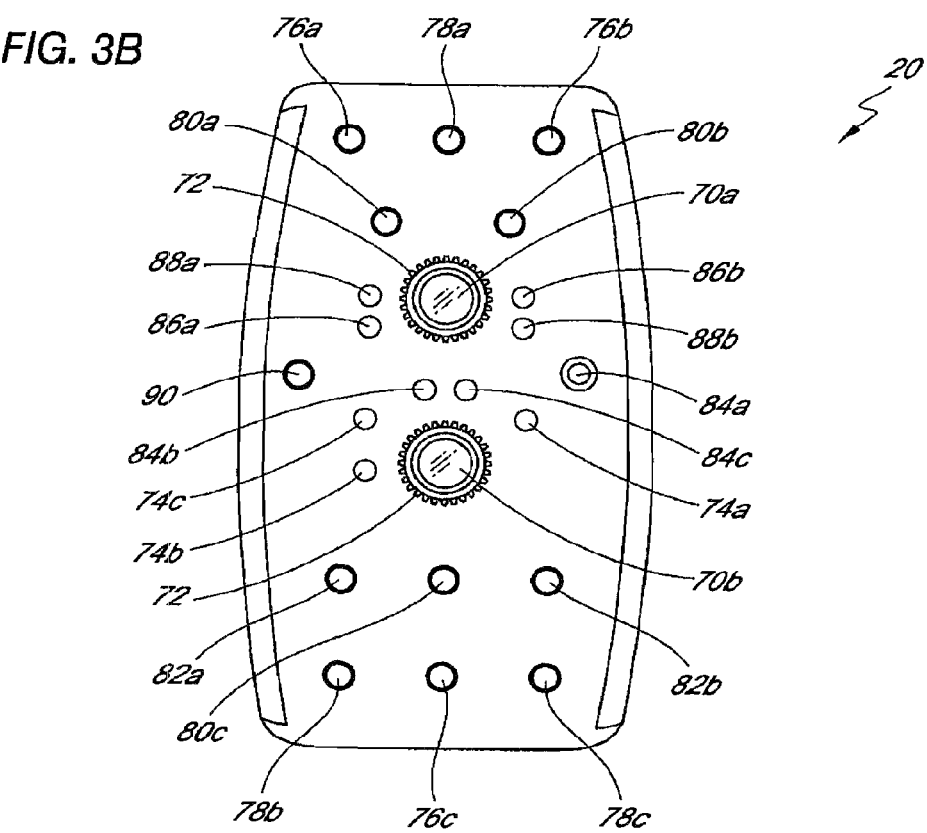
FIG. 3B is a bottom view of one embodiment of the counterfeit drug-detecting LED device of the present invention.

Also disposed on and/or within the housing are ultraviolet, infrared and white light momentary push buttons 54*a-e* which turn on and off certain light sources on the bottom of the housing (discussed in reference to FIG. 3B below) corresponding to the buttons. The housing also includes an on-off switch 56 and an illumination intensity control 58 which is connected to a subset of, or possibly all of, the light sources. UV-Visible momentary push-buttons 60*a-d* turn on and off certain light sources on the bottom of the housing (FIG. 3B).

Video output 62 interfaces with USB and power supply connections. Image capture or video capture may occur through the USB connection. In the device shown in FIG. 3A, button 54*a* controls a white light source used for normal light illumination, and buttons 54*b-e* control LEDs having center wavelengths of about 351 nm, about 800 nm, about 900 nm, and about 1050 nm, respectively. It will be appreciated that the such light sources are not pure, but emit in a wavelength band centered at or near the recited center wavelength. The bandwidth is not particularly critical to device function. It should be recognized that LED light sources with the recited center wavelengths and having suitable bandwidths are commercially available.

A "white" light source can contain a set of narrowband emissions at different locations in the visible spectrum or can have a flatter broadband emission spectrum across most or all of the visible range.

In addition, referring to FIG. 3A, UV-Visible momentary push buttons 12*a-d* control light sources having center wavelengths of about 525 nm, about 470 nm, about 455 nm, and about 405 nm, respectively. An illumination intensity control 58 may be provided to provide intensity adjustability for low or highly reflective surfaces.

Referring to FIG. 3B, the bottom of the housing includes two high sensitivity CCD chips (cameras) 70*a* and 70*b*, either or both of which may contain a removable color lens filter, which, in one embodiment, is held in place by a rubber grommet 72. Although CCD chips are exemplified herein, the device can comprise any light sensitive device as are know to those skilled in the art such as photodiodes or the like. In further embodiments, the camera lenses are dismountable, high quality precision ground, multi-element glass micro-board lenses which results in chromatic aberration reduction. The device 20 is usable with one or both color filters in place, or is usable without filters. As indicate herein, in some embodiments, the device does not comprise a display or an image acquisition device (e.g., CCD chip).

In more particular exemplary embodiments, the arrangement of the LEDs in FIG. 3B is as follows: 351 nm (74*a-c*), 405 nm (76*a-c*), 455 nm (78*a-c*), 470 nm (80*a-c*), 525 nm (82*a-b*), 800 nm (84*a-c*), 900 nm (86*a-b*), 1050 nm (88*a-b*) and white light (90). The 351 nm LEDs are generally of lower output power than the 405-800 nm LEDs. The 900 nm and 1050 nm LEDs emit light in the infrared region, while the 351 nm LEDs emit light in the ultraviolet region. These wavelengths are illustrative of a particular exemplary embodiment. Thus, it is within the scope of the present invention to utilize other wavelengths and/or wavelength combinations that are more appropriate for scanning and evaluating particular pharmaceutical and/or packaging or packaging components.

The detection device 20 including the control circuitry is configurable so as to provide simultaneous multiple light source illumination capability for various specific analysis requirements. It will be appreciated that the arrangement of buttons/controls shown in FIG. 3A, and LEDs shown in FIG. 3B, are exemplary, and many variations of these can occur and are within the scope of the present invention. In addition, the invention also is not limited to the particular wavelengths mentioned above. Many variations of these can be used, and are also within the scope of the present invention.

The detection device 20 described herein is ergonomically designed for hand-held comfort, is portable and lightweight, and fits inside a shirt or jacket pocket. Thus, it is well suited for work in the field, and obviates the need to send field samples to a laboratory for analysis. Thus, customs agents can quickly determine whether a suspect pharmaceutical is in fact counterfeit. If desired, the suspected counterfeit pharmaceutical can be subjected to further confirmatory testing using conventional methods.

Figure 5:
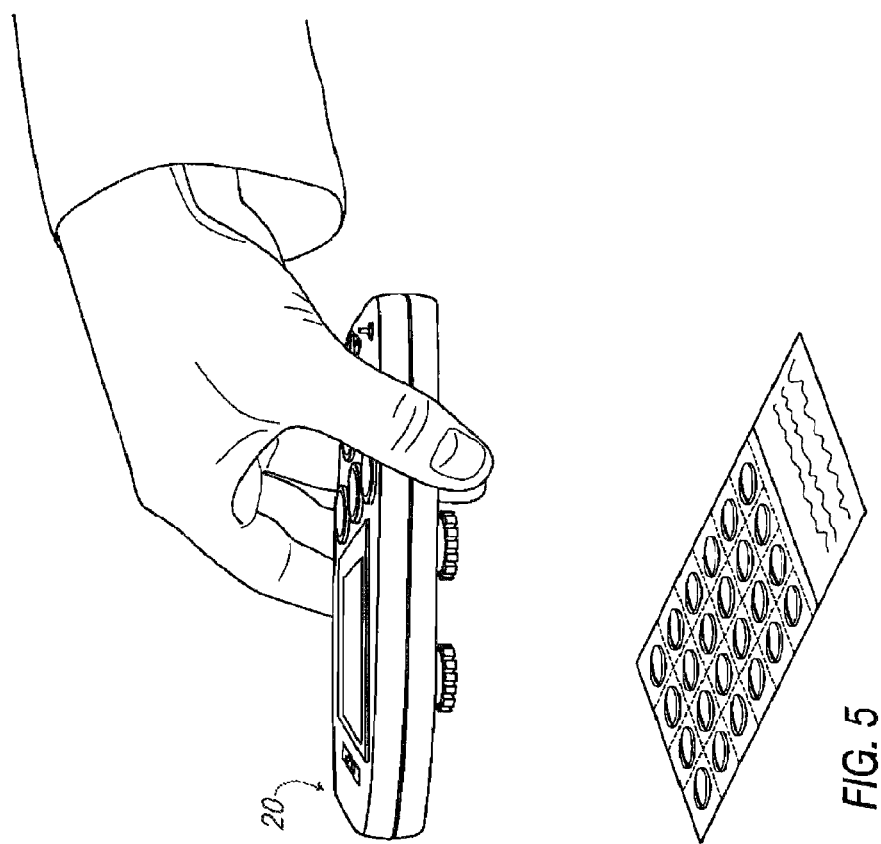
FIG. 5 is a diagram of the counterfeit drug-detecting LED device in use with tablets in their packaging.

Now referring to FIGS. 4 and 5 which are diagrams showing the device in use for detection of suspected counterfeit pharmaceutical products both out of (FIG. 4) and in (FIG. 5) the packaging material and also to FIG. 6, which is a high level flow diagram of an illustrative embodiment of the methodology of the present invention. When a user is to conduct an examination of a suspect product or packaging, the user undertakes the steps necessary to establish the scanning protocol that will be used to determine if the suspect product is an authentic product or a counterfeit, Step 300. The user initially determines the light sources having the wavelengths of light that should be used during such scanning so as to create the potential for determining from such a light scanning process if the suspect product is authentic or not. In addition, the user determines if the light returning from the illuminated object(s) should be filtered or appropriately treated in conjunction with an direct viewing by the user or viewing via an image acquisition device. As provided herein, in an embodiment of the present invention the suspect product or the suspect product and authentic product are viewed at the same time by a user that is wearing colored goggles or glasses.

If image acquisition devices are being utilized to acquire image data representative of the returning light (color and/or brightness) the user determines which of such devices should be used and in combination with what illuminating light sources. As provided herein, in an embodiment of the present invention filters (e.g., colored filters) are placed over one or both camera lenses comprising the image acquisition devices. Thus, the user determines the appropriate filtering. It should be noted that the device may contain no camera or display, a single camera, two cameras, or three or more cameras, and that the presence of two cameras is only exemplary.

Also, the user can determine if the detection device should be oriented so as to be at an angle with respect to the object(s) being illuminated. For example, holding the detection device at oblique angles in some cases allow for better imaging/scanning analysis.

In sum, the user determines at the outset the light sources, the light illumination sequencing, the image acquisition devices and other control parameters and the like that should be utilized to scan the suspect product/packaging and taking the appropriate steps so that scanning is done according to the determined protocol.

After establishing the protocol and setting up the detection device, the user locates the detection device in proximity to the suspect product, and in the case where the protocol includes simultaneously scanning the suspect and authentic product, locates the device in proximity to both of them, Step 310. For example and as shown in FIGS. 4-5, the detection device 20 is held above the suspected counterfeit pharmaceutical product (FIG. 4) and/or product packaging (FIG. 5) by the user. In addition, the user can orient the detection device with respect to the object(s) to be illuminated in cases where better imaging and the like would be achievable.

If it is next determined if the process is proceeding with simultaneously viewing of the suspect and authentic product or not, Step 320. In the case where a suspected counterfeit pharmaceutical product and the corresponding authentic product (and/or product packaging) are placed side by side (Yes, Step 320), the suspect product and the authentic product are illuminated with the detection device 20 using one or more wavelengths of visible, ultraviolet or white light, Step 340 and and differences in color and/or brightness of the authentic and suspected pharmaceutical products are observed or viewed by the user, Step 350. In an illustrative exemplary embodiment, the authentic and suspected pharmaceutical products and/or packaging are viewed under white light and light having a specific wavelength (e.g., 405, 455, 470 or 525 nm). As indicated herein, such viewing can be achieved by the user directly viewing the authentic and suspected pharmaceutical products and/or packaging while they are being illuminated and observing the appearance of both as they are being simultaneously illuminated. Alternatively, the appearance of the authentic and suspected pharmaceutical products and/or packaging are observed by viewing the appropriate LCD display screen 36.

The images of the two samples under the two different lighting conditions are then compared or the appearances of the samples are then compared, Step 360. Thereafter a determination is made whether or not the scanning protocol is completed, Step 390. If the process is not complete (No, Step 390), the process proceeds to illuminating or exposing at another set of wavelengths according to the protocol and steps 350 and 360 repeated as many times until it is determined that the process is complete (Yes, Step 390). If the process is determine to be complete, and if differences were observed from observing the appearance of the samples; such differences are evaluated to determine if they are representative of a suspected counterfeit, Step 400.

On the other hand, if it is next determined that the process is not proceeding with simultaneously viewing of the suspect and authentic product (No, Step 320), then the process proceeds with acquiring reference information that is representative of the authentic product, Step 330. For example, the control circuitry 26 retrieves information (acquired image data for the authentic product) from the memory 38 so it can be utilized later in the process. In this embodiment, the suspected counterfeit product is viewed alone, thus the suspected counterfeit product is illuminated with the detection device 20 using one or more wavelengths of visible, ultraviolet or white light, Step 340 and image data is acquired using the image acquisition devices, Step 370.

Thereafter, the acquired image data or image is then compared to the retrieved pre-existing image of the corresponding authentic product under the same illumination and detection conditions, Step 380. In this way, an agent in the field need not carry authentic samples of pharmaceutical products and or packaging with them as well as avoiding the need to take appropriate steps to maintain the authentic products so that they do not degrade, break down or otherwise become unusable as a reference sample.

In further embodiments the user would refer to the reference image one of before or after acquisition of the image for the suspect product and perform a comparison of the acquired image for the suspect product with reference image that was viewed before or after. In yet another embodiment and as provided herein, the control circuitry 26 controls the operation of the display 36 so that the reference image and the acquired image of the suspect product are viewed simultaneously by the user. In other words, the two images are compared or the appearances of the images are compared.

Thereafter a determination is made whether or not the scanning protocol is completed, Step 390. If the process is not complete (No, Step 390), the process proceeds to illuminating or exposing the suspect product to another set of wavelengths according to the protocol and Steps 340, 370 and 380 are repeated as many times until it is determined that the process is complete (Yes, Step 390). If the process is determine to be complete, and if differences were observed from the performed comparison; such differences are evaluated to determine if they are representative of a suspected counterfeit, Step 400.

Although a preferred embodiment of the invention has been described using specific terms, such description is for illustrative purposes only, and it is to be understood that changes and variations may be made without departing from the spirit or scope of the following claims.

INCORPORATION BY REFERENCE

All patents, published patent applications and other references disclosed herein are hereby expressly incorporated by reference in their entireties by reference.

EQUIVALENTS

Those skilled in the art will recognize, or be able to ascertain using no more than routine experimentation, many equivalents of the specific embodiments of the invention described herein. Such equivalents are intended to be encompassed by the following claims.

What is claimed is:

1. A device for detecting a counterfeit product, comprising:
   a plurality of light sources configured to emit light at a plurality of different wavelengths onto a potentially suspect product;
   at least one image acquisition device; and
   at least one display for observing a color comparison of an image of the potentially suspect product illuminated by the plurality of different wavelengths and an image of a known product under illumination of the same wavelengths.

2. The device of claim 1 further comprising a housing and wherein the plurality of light sources and the at least one image acquisition device are coupled to the housing so that the plurality of light sources and the at least one image acquisition device are maintained in fixed relation to each other while the potentially suspect product is being illuminated.

3. The device of claim 2, wherein the plurality of light sources and the at least one image acquisition device are on a bottom of the housing, and the at least one display is on a top of the housing.

4. The device of claim 1, further comprising a light source control device for controlling respective ones of the light sources.

5. The device of claim 1, further comprising a communication device configured so as to allow communications between the detection device and a device that is external to the detection device.

6. The device of claim 1, wherein the device further comprises two image acquisition devices.

7. The device of claim 1, wherein said image acquisition device includes a colored filter.

8. The device of claim 1, wherein said image acquisition device is a CCD array.

9. The device of claim 1, wherein at least one of the plurality of light sources is configured so as to emit light having an infrared wavelength, at least one of the plurality of light sources is configured so as to emit light having a visible wavelength, and at least one of the plurality of light sources is configured so as to emit light having an ultraviolet wavelength.

10. The device of claim 1, wherein said light sources are LED light sources.

11. The device of claim 1, wherein the at least one image acquisition device includes a macro lens.

12. A device for detecting a counterfeit product, comprising:
   a housing;
   a plurality of light sources coupled to said housing configured to emit light at a plurality of different wavelengths, wherein said light sources includes at least one infrared wavelength, at least one visible wavelength and at least one ultraviolet wavelength;
   at least one image acquisition device for acquiring an image of potentially suspect product illuminated by the plurality of different wavelengths;
   at least one display for observing a color comparison of the image of the potentially suspect product illuminated by the plurality of different wavelengths and an image of a known product under illumination of the same wavelengths; and
   a plurality of buttons controlling respective ones of said light sources.

13. A method for detecting a counterfeit product, comprising the steps of:
   selecting a wavelength or wavelength range of light;
   exposing a suspected counterfeit product to light of said selected wavelength or wavelength range with a light source;
   viewing a color of said suspected counterfeit product upon exposure to said wavelength or wavelength range;
   comparing the color of said suspected counterfeit product exposed to the wavelength or wavelength range to a color of a known product exposed to light of the same wavelength or wavelength range; and
   determining a similarity of a composition between the suspected counterfeit product and the known product without viewing a light sensitive marker.

14. The method of claim 13, further comprising wearing colored goggles when viewing the suspected counterfeit product.

15. The method of claim 13, wherein said wavelength is within the visible, ultraviolet or infrared range.

16. The method of claim 13, wherein the suspected counterfeit product and said known product are exposed to said light and viewed simultaneously.

17. The method of claim 13, wherein the appearance of the suspected counterfeit product is compared to an image of the known product exposed to the same wavelength of light.

18. The method of claim 13, wherein said suspected counterfeit product is a tablet, capsule, vial and/or packaging components.

19. The method of claim 13, wherein exposing the suspected counterfeit product to light further comprises turning a plurality of light sources on and off in a predetermined sequence.

20. The method of claim 13, wherein determining the similarity of the composition further comprises detecting a component within the suspected counterfeit product based at least in part on a difference between a color of the suspected counterfeit product and a color of the known product.

21. The method of claim 20, wherein the component is an excipient.

22. The method of claim 20, wherein the color difference between the suspected counterfeit product and the known product is not detectable under ambient lighting conditions.

* * * * *